(12) United States Patent
Al-Ali

(10) Patent No.: US 7,030,749 B2
(45) Date of Patent: *Apr. 18, 2006

(54) PARALLEL MEASUREMENT ALARM PROCESSOR

(75) Inventor: Ammar Al-Ali, Tustin, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/975,860

(22) Filed: Oct. 28, 2004

(65) Prior Publication Data

US 2005/0083193 A1 Apr. 21, 2005

Related U.S. Application Data

(63) Continuation of application No. 10/351,735, filed on Jan. 24, 2003, now Pat. No. 6,822,564.

(60) Provisional application No. 60/351,510, filed on Jan. 24, 2002.

(51) Int. Cl.
*G08B 29/00* (2006.01)

(52) U.S. Cl. .............. 340/511; 340/507; 340/521; 340/573.1; 600/300; 600/301; 700/10; 700/14; 702/119

(58) Field of Classification Search .......... 340/507, 340/511, 521, 573.1; 600/300, 301, 322–326; 700/10, 14, 79; 702/119
See application file for complete search history.

(56) References Cited

U.S. PATENT DOCUMENTS

| | | |
|---|---|---|
| 4,245,648 A | 1/1981 | Trimmer et al. |
| 4,960,128 A | 10/1990 | Gordon et al. |
| 5,163,438 A | 11/1992 | Gordon et al. |
| 5,298,021 A | 3/1994 | Sherer |
| 5,337,744 A | 8/1994 | Branigan |
| 5,431,170 A | 7/1995 | Mathews |
| 5,452,717 A | 9/1995 | Branigan et al. |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,590,649 A | 1/1997 | Caro et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,819,007 A | 10/1998 | Elghazzawi |
| 5,823,950 A | 10/1998 | Diab et al. |
| 5,830,131 A | 11/1998 | Caro et al. |
| 5,833,618 A | 11/1998 | Caro et al. |
| 5,860,918 A | 1/1999 | Schradi et al. |
| 5,860,919 A | 1/1999 | Kiani-Azarbayjany et al. |
| 5,890,929 A | 4/1999 | Mills et al. |

(Continued)

*Primary Examiner*—Daniel Wu
*Assistant Examiner*—Samuel J. Walk
(74) *Attorney, Agent, or Firm*—Knobbe, Martens, Olson & Bear, LLP

(57) ABSTRACT

An alarm processor suppresses alarms when a physiological parameter is below a predetermined value but recovering toward a normal range.

11 Claims, 9 Drawing Sheets

U.S. PATENT DOCUMENTS

| | | |
|---|---|---|
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,236,872 B1 | 5/2001 | Diab et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,331,159 B1 | 12/2001 | Amano et al. |
| 6,334,065 B1 | 12/2001 | Al-Ali et al. |
| 6,349,228 B1 | 2/2002 | Kiani et al. |
| 6,360,114 B1 | 3/2002 | Diab et al. |
| 6,371,921 B1 | 4/2002 | Caro et al. |
| 6,377,829 B1 | 4/2002 | Al-Ali |
| 6,388,240 B1 | 5/2002 | Schulz et al. |
| 6,397,091 B1 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B1 | 12/2002 | Diab et al. |
| 6,515,273 B1 | 2/2003 | Al-Ali |
| 6,525,386 B1 | 2/2003 | Mills et al. |
| 6,526,300 B1 | 2/2003 | Kiani et al. |
| 6,537,214 B1 | 3/2003 | Hood et al. |
| 6,541,756 B1 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,597,933 B1 | 7/2003 | Kiani et al. |
| 6,606,511 B1 | 8/2003 | Ali et al. |
| 6,632,181 B1 | 10/2003 | Flaherty et al. |
| 6,640,116 B1 | 10/2003 | Diab |
| 6,643,530 B1 | 11/2003 | Diab et al. |
| 6,650,917 B1 | 11/2003 | Diab et al. |
| 6,654,624 B1 | 11/2003 | Diab et al. |
| 6,658,276 B1 | 12/2003 | Kianl et al. |
| 6,671,531 B1 | 12/2003 | Al-Ali et al. |
| 6,678,543 B1 | 1/2004 | Diab et al. |
| 6,684,090 B1 | 1/2004 | Ali et al. |
| 6,697,656 B1 | 2/2004 | Al-Ali |
| 6,697,658 B1 | 2/2004 | Al-Ali |
| RE38,476 E | 3/2004 | Diab et al. |
| 6,699,194 B1 | 3/2004 | Diab et al. |
| 6,714,804 B1 | 3/2004 | Al-Ali et al. |
| RE38,492 E | 4/2004 | Diab et al. |
| 6,725,075 B1 | 4/2004 | Al-Ali |
| 6,745,060 B1 | 6/2004 | Diab et al. |
| 6,760,607 B1 | 7/2004 | Al-All |
| 6,770,028 B1 | 8/2004 | Ali et al. |
| 6,771,994 B1 | 8/2004 | Kiani et al. |
| 6,792,300 B1 | 9/2004 | Diab et al. |
| 2003/0004421 A1 | 1/2003 | Ting et al. |
| 2003/0107487 A1 | 6/2003 | Korman et al. |

PARALLEL MEASUREMENT ALARM PROCESSOR

CROSS REFERENCE TO RELATED APPLICATION

The present application claims priority benefit under 35 U.S.C. § 120 to, and is a continuation of, U.S. patent application Ser. No. 10/351,735, filed Jan. 24, 2003, now U.S. Pat. No. 6,822,564 entitled "*Parallel Measurement Alarm Processor,*" which claims priority benefit under 35 U.S.C. § 119(e) from U.S. Provisional Application No. 60/351,510, filed Jan. 24, 2002, entitled "*Parallel Measurement Alarm Processor.*" The present application also incorporates the foregoing utility disclosure herein by reference.

BACKGROUND OF THE INVENTION

Physiological measurement instruments employed in healthcare environments often feature visual and audible alarm mechanisms that alert a caregiver when a patient's vital signs are outside of predetermined limits. One example is a pulse oximeter, which measures the oxygen saturation level of arterial blood, an indicator of oxygen supply. A typical pulse oximeter displays a numerical readout of the patient's oxygen saturation, a numerical readout of pulse rate, and a plethysmograph, which is indicative of a patient's pulse. In addition, a pulse oximeter provides an alarm that warns of a potential desaturation event.

FIG. 1 illustrates a prior art pulse oximeter portion 100 having a signal input 101 and generating an oxygen saturation measurement output 103 and an alarm output 105. The pulse oximeter portion 100 has an oxygen saturation ($SpO_2$) processor 110 and an associated threshold detector 120. The $SpO_2$ processor 110 derives an oxygen saturation measurement from the signal input 101. The signal input 101 is typically an amplified, filtered, digitized and demodulated sensor signal. A sensor emits both red and infrared (IR) wavelength light, which is transmitted through a patient's tissue, detected and input to the pulse oximeter. The pulse oximeter calculates a normalized ratio (AC/DC) of the detected red and infrared intensities, and an arterial oxygen saturation value is empirically determined based on a ratio of these normalized ratios, as is well-known in the art. The oxygen saturation measurement output 103 is typically a digital signal that is then communicated to a display.

FIG. 2 illustrates the operation of a conventional threshold detector 120 (FIG. 1) utilizing a graph 200 of oxygen saturation 201 versus time 202. The graph 200 displays a particular oxygen saturation measurement 210 corresponding to the measurement output 103 (FIG. 1) and a predetermined alarm threshold 206. During an alarm time period 270 when the measured oxygen saturation 210 is below the threshold 206, an alarm output 105 (FIG. 1) is generated, which triggers a caregiver alert. Adjusting the threshold 206 to a lower value of oxygen saturation 201 reduces the probability of an alarm, i.e. reduces the probability of a false alarm and increases the probability of a missed event. Likewise, adjusting the threshold 206 to a higher value of oxygen saturation 201 increases the probability of an alarm, i.e. increases the probability of a false alarm and decreases the probability of a missed event.

SUMMARY OF THE INVENTION

One performance measure for a physiological measurement instrument is the probability of a false alarm compared with the probability of a missed event. Missed events, such as an oxygen desaturation when measuring oxygen saturation, may detrimentally effect patient health. False alarms waste caregiver resources and may also result in a true alarm being ignored. It is desirable, therefore, to provide an alarm mechanism to reduce the probability of false alarms without significantly increasing the probability of missed events, and, similarly, to reduce the probability of missed events without significantly increasing the probability of false alarms.

An alarm processor has a signal input responsive to a physiological parameter and a plurality of parameter processors responsive to the signal input so as to provide a plurality of measurements of the parameter having differing characteristics. In addition, the alarm processor has an alarm condition applicable to at least one of the measurements so as to define a limit for the parameter. Further, the alarm processor has an alarm indicator operating on the measurements and the alarm condition so as to provide an alarm output that changes state to indicate that the parameter may have exceeded the limit.

DETAILED DESCRIPTION OF THE PREFERRED EMBODIMENT

Figure 3:
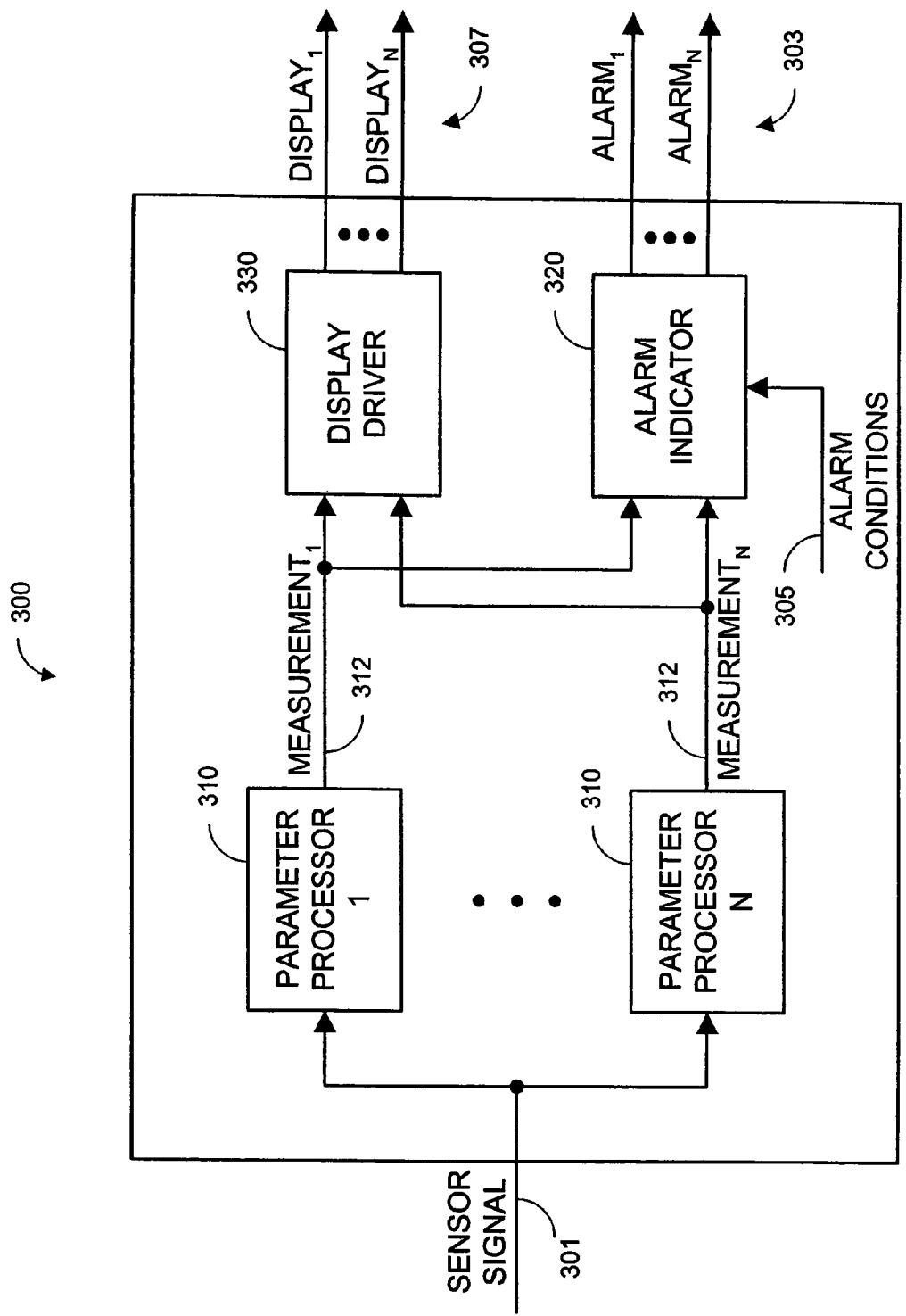
FIG. 3 is a block diagram of an alarm processor utilizing parallel measurements of a physiological parameter.

FIG. 3 illustrates a parallel measurement alarm processor 300. The alarm processor 300 has a sensor signal input 301 responsive to a physiological parameter and provides one or more alarm outputs 303 to indicate that the physiological parameter may have exceeded particular limits. The alarm processor 300 also has multiple parameter processors 310, which do not necessarily have the same or similar internal configurations. The multiple parameter processors 310 input the sensor signal 301 and provide parallel measurements 312 of the physiological parameter, each measurement having differing characteristics, such as response time or bandwidth to name a few. The alarm processor 300 further has an alarm indicator 320 that inputs the parallel parameter measurements 312 and generates the alarm outputs 303 based upon alarm conditions 305. The alarm outputs 303 change state to indicate that the parameter may have exceed one or more limits and to trigger an alarm accordingly. The alarm conditions 305 define particular limits with respect to one or more of the measurements 312. The alarm conditions 305 may be predefined, such as by user input, or determined by a separate process, such as a measurement of sensor signal quality or data confidence as described in U.S. patent application Ser. No. 09/858,114 entitled "Pulse Oximetry Data Confidence Indicator," assigned to Masimo Corporation, Irvine, Calif. and incorporated by reference herein. The alarm processer 300 may also have a display driver 330 that processes one or more of the parameter measurements 312 and provides one or more display outputs 307.

Figure 1:
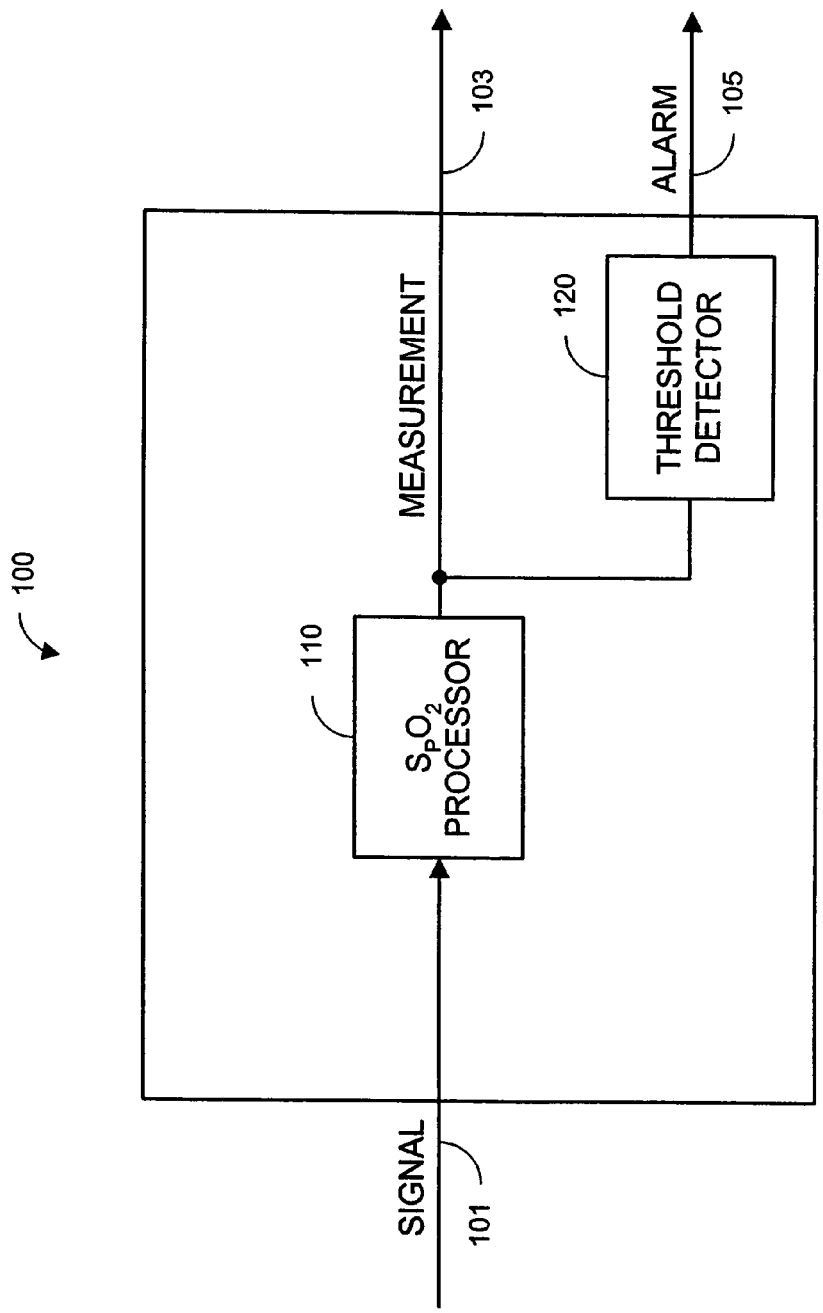
FIG. 1 is a block diagram of a prior art pulse oximeter portion.
Figure 2:
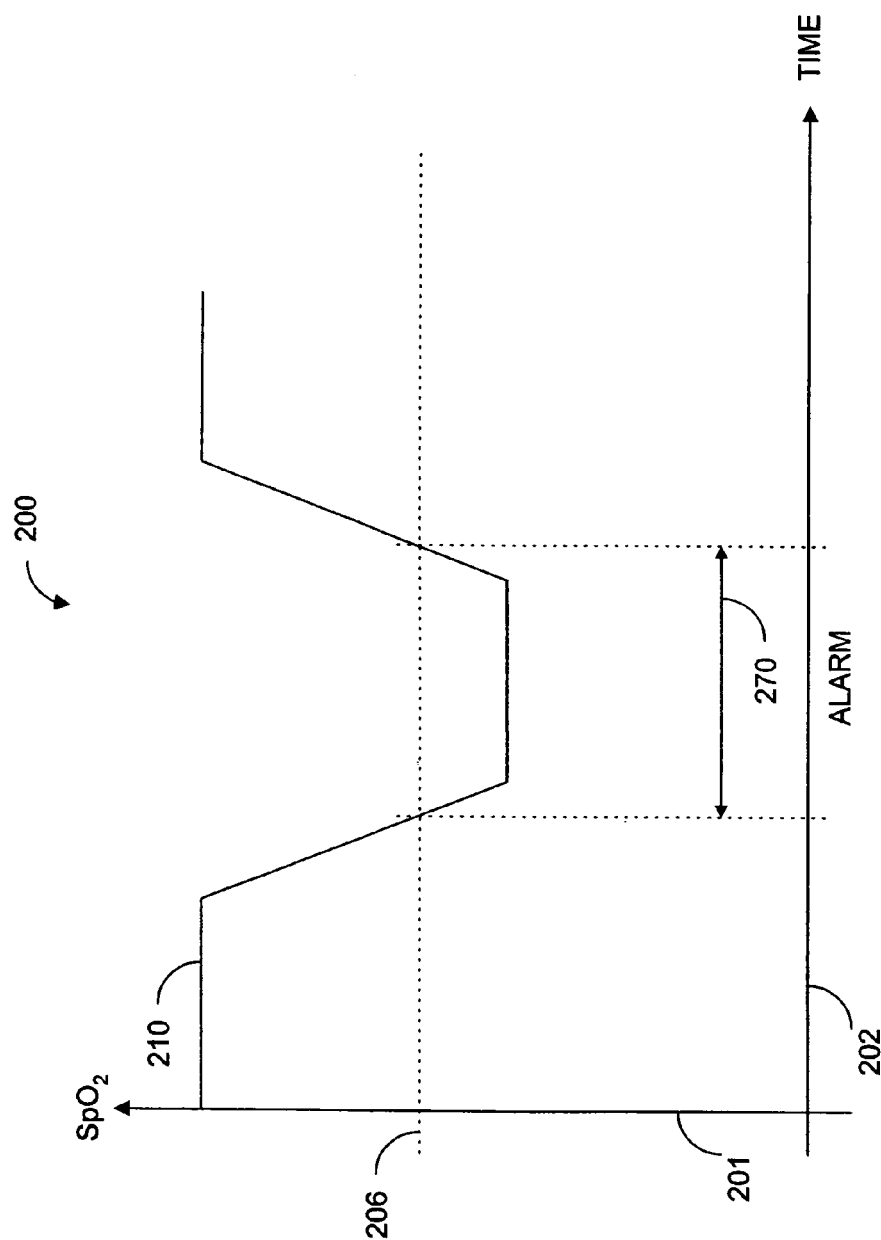
FIG. 2 is a graph of oxygen saturation versus time illustrating a conventional threshold detector alarm.
Figure 4:
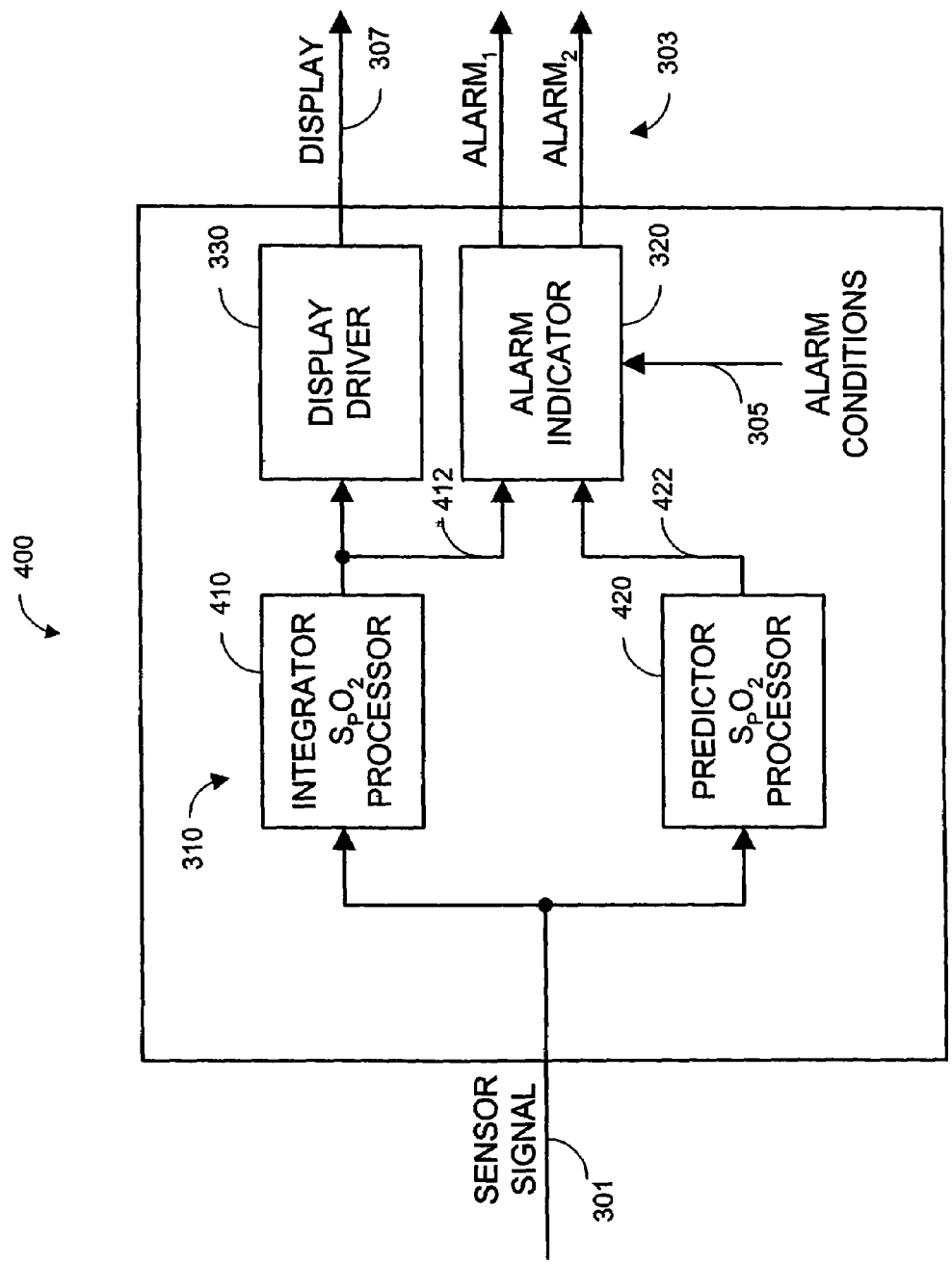
FIG. 4 is a block diagram of a pulse oximeter processor utilizing dual oxygen saturation measurements.

FIG. 4 illustrates a pulse oximeter embodiment 400 of the alarm processor 300 (FIG. 3) described above. A pulse oximeter sensor (not shown) provides a signal input 301 responsive to arterial oxygen saturation, as described with respect to FIG. 1, above. The alarm processor 400 has dual oxygen saturation processors 310. An integrator oxygen saturation ($SpO_2$) processor 410 outputs a slow $SpO_2$ measurement 412, i.e. a measurement having a slow response time to changes in the $SpO_2$ parameter. A predictor $SpO_2$ processor 420 outputs a fast $SpO_2$ measurement 422, i.e. a measurement having a fast response time that tracks changes in the $SpO_2$ parameter. The slow $SpO_2$ measurement 412 is input to a display driver 330, which provides an oxygen saturation display output 307. For example, the display output 307 may be input to a digital display that provides a numerical readout of oxygen saturation to a caregiver. Both the slow $SpO_2$ measurement 412 and the fast $SpO_2$ measurement 422 are input to an alarm indicator 320 that generates at least one alarm output 303 based upon alarm conditions 305, as described in further detail with respect to FIGS. 5-8, below.

The integrator $SpO_2$ processor 410, advantageously, provides a smoothed measurement of oxygen saturation suitable for threshold detection. The predictor $SpO_2$ processor 420, advantageously, provides a curve-fitting or a predictive measurement of oxygen saturation that detects trends in oxygen saturation, as described in further detail with respect to FIG. 5 and FIGS. 6A–B, below. Further, the predictor $SpO_2$ processor 420 advantageously tracks oxygen saturation details that may signal a critical physiological event, as described in further detail with respect to FIGS. 7–8, below. The integrator $SpO_2$ processor 410 and predictor $SpO_2$ processor 420 may be a pulse oximeter as described in U.S. patent application Ser. No. 09/586,845 entitled "Variable Mode Averager," assigned to Masimo Corporation, Irvine, Calif. and incorporated by reference herein.

Figure 5:
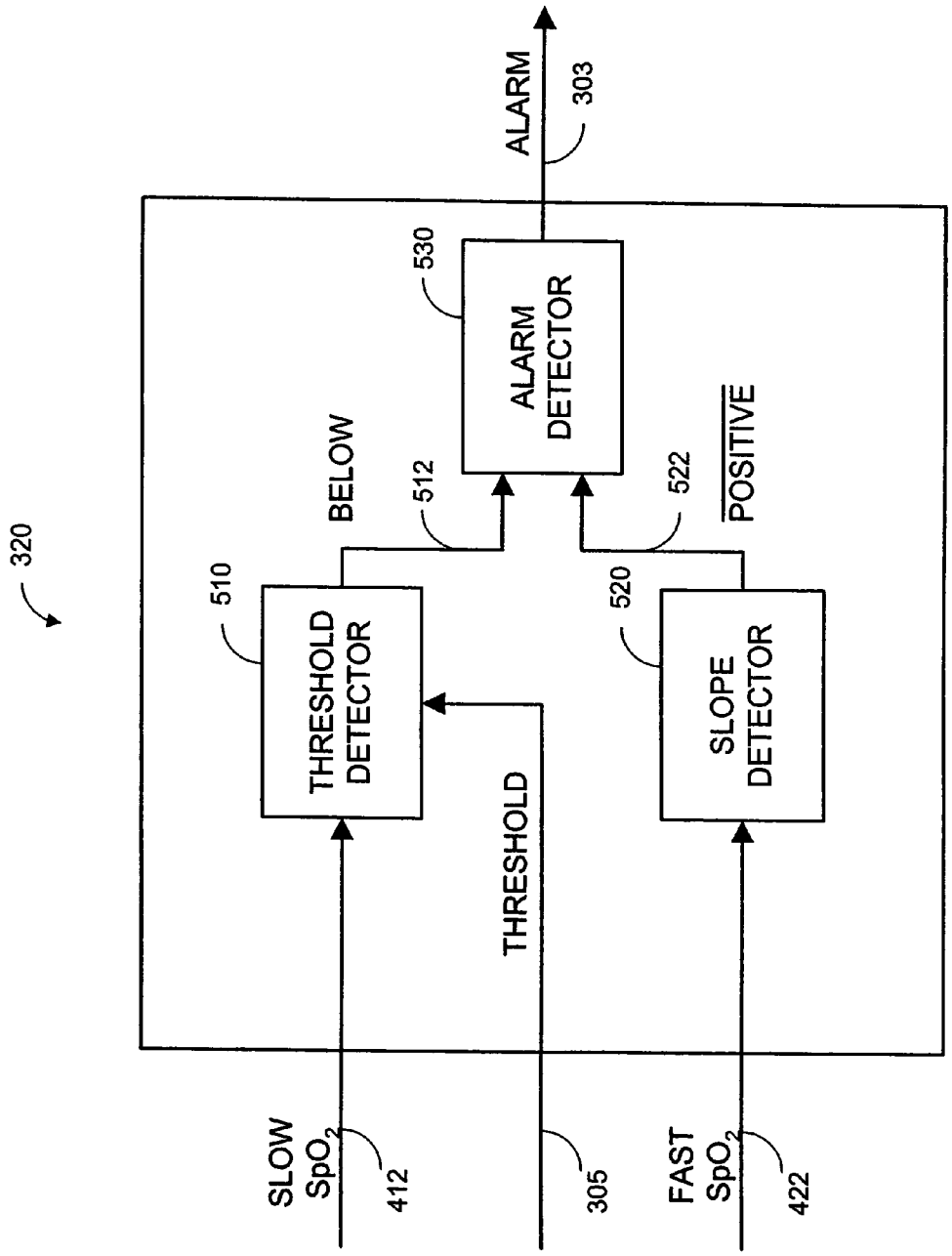
FIG. 5 is a block diagram of a predictive alarm indicator utilizing a threshold detector with a slow oxygen saturation measurement input and a slope detector with a fast oxygen saturation measurement input.

FIG. 5 illustrates a trend embodiment of an alarm indicator 320, which has a threshold detector 510, a slope detector 520 and alarm detector 530. The threshold detector 510 has a slow $SpO_2$ measurement 412 and a threshold alarm condition 305 as inputs and a logic output BELOW 512. The slope detector 520 has a fast $SpO_2$ measurement 422 input and a logic output POSITIVE/522. The alarm detector 530 has BELOW 512 and POSITIVE/522 logic inputs and generates an alarm output 303. The threshold detector 510 is a comparator that asserts BELOW 512 while the slow $SpO_2$ measurement 412 is less in value than the value of the threshold 305. The slope detector 520 is a differentiator and comparator that asserts POSITIVE/522 while the slope of the fast $SpO_2$ measurement 422 is non-positive, i.e. while the derivative of the fast $SpO_2$ measurement 422 is zero or less than zero. The alarm detector 530 performs a logical AND function, asserting the alarm output 303 and indicating an alarm when BELOW 512 and POSITIVE/522 are both asserted. In this manner, an alarm output 303 only changes state when the slow $SpO_2$ measurement 412 is below a threshold 305 and the fast $SpO_2$ measurement 422 has not begun to increase in value. Advantageously, the trend recognition alarm indicator 320 reduces false alarms by suppressing a threshold-based alarm on the slow $SpO_2$ measurement 412 when the fast $SpO_2$ measurement 422 determines that a patient's oxygen saturation is in recovery, as described in further detail with respect to FIGS. 6A–B, below.

Figure 6A:
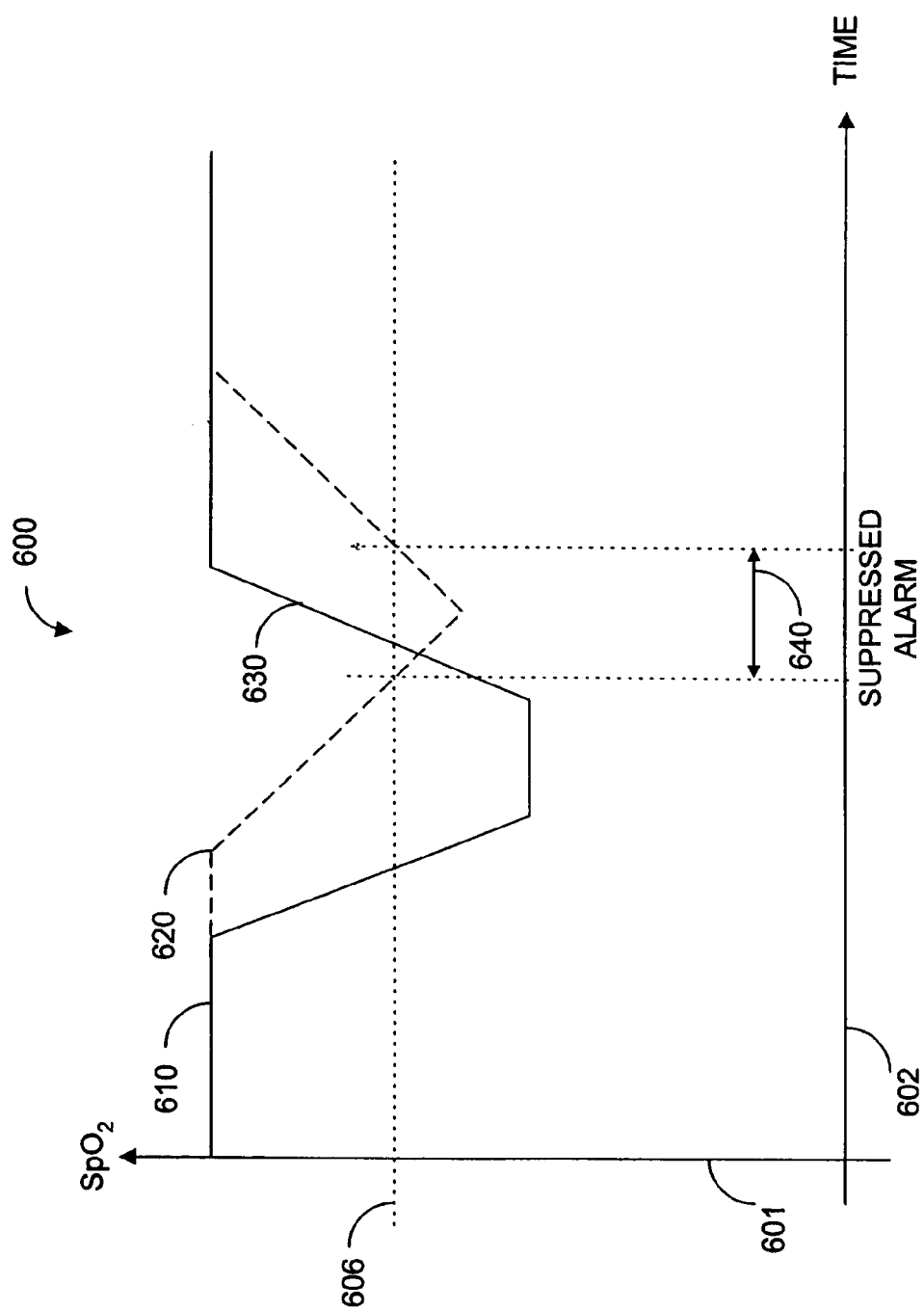
FIGS. 6A–B are graphs of oxygen saturation versus time illustrating operation of the alarm indicator according to FIG. 5.
Figure 6B:
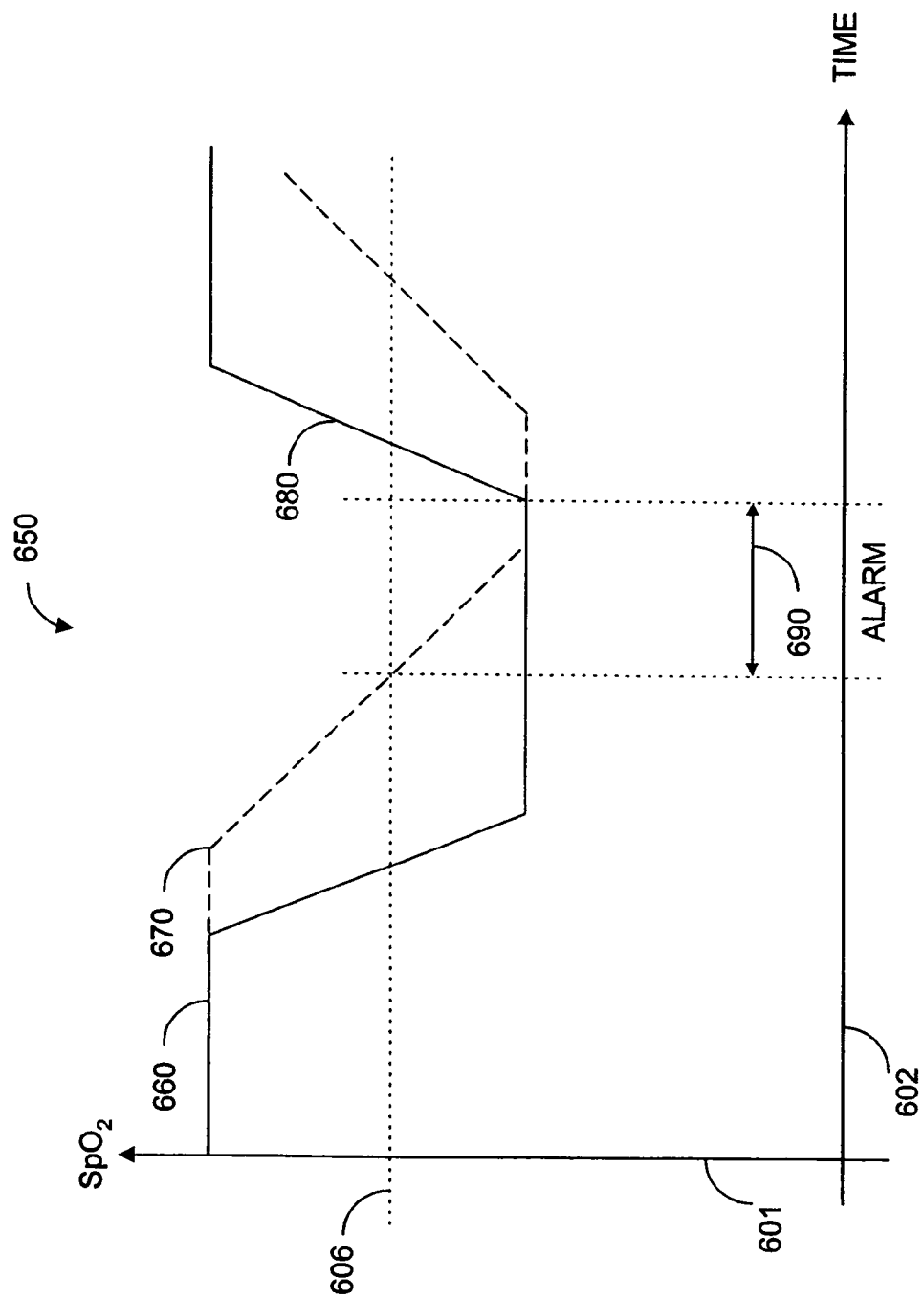

FIGS. 6A–B illustrate operation of the trend recognition alarm indicator 320 (FIG. 5). In FIG. 6A, a graph 600 has an $SpO_2$ axis 601 and a time axis 602. Shown along the $SpO_2$ axis 601 is a constant $SpO_2$ value 606 corresponding to a threshold 305 (FIG. 5). The graph 600 shows a first plot of $SpO_2$ versus time 610 corresponding to a fast $SpO_2$ measurement 422 (FIG. 5). The graph 600 also shows a second plot of $SpO_2$ versus time 620 corresponding to a slow $SpO_2$ measurement 412 (FIG. 5). A suppressed alarm interval 640 along the time axis 602 corresponds to an alarm that would be indicated by the threshold detector 510 (FIG. 5) but is suppressed as occurring during a positive slope portion 630 of a fast $SpO_2$ measurement 610. The alarm detector 530 (FIG. 5) would not assert an alarm output 303 (FIG. 5) during this interval.

In FIG. 6B, a graph 650 shows a first plot of $SpO_2$ versus time 660 corresponding to a fast $SpO_2$ measurement 422 (FIG. 5). The graph 650 also shows a second plot of $SpO_2$ versus time 670 corresponding to a slow $SpO_2$ measurement 412 (FIG. 5). An alarm interval 690 along the time axis 602 corresponds to an alarm period triggered by the alarm output 303 (FIG. 5). This alarm interval 640 occurs while a slow $SpO_2$ measurement 670 is below the threshold 606 and before a positive slope portion 680 of a fast $SpO_2$ measurement 660.

Figure 7:
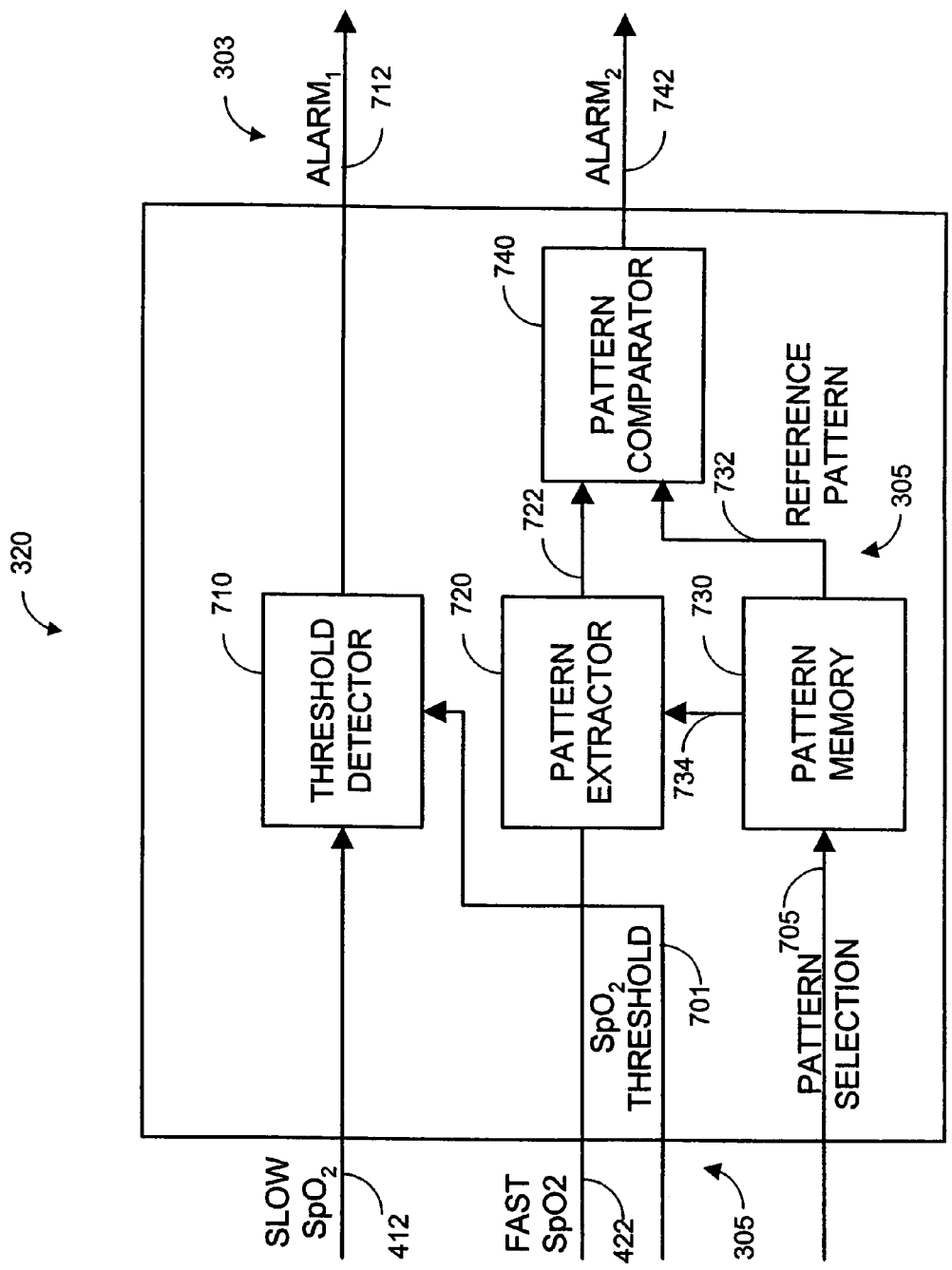
FIG. 7 is a block diagram of a pattern recognition alarm indicator utilizing a threshold detector with a slow oxygen saturation measurement input and a pattern extractor with a fast oxygen saturation measurement input.

FIG. 7 illustrates a pattern recognition embodiment of an alarm indicator 320, having a threshold detector 710, a pattern extractor 720, a pattern memory 730 and a pattern comparator 740. Further, the alarm indicator 320 has slow $SpO_2$ 412 and fast $SpO_2$ 422 measurement inputs in addition to threshold 701 and reference pattern 732 alarm condition inputs 305. The threshold detector 710 has a slow $SpO_2$ measurement 412 and a $SpO_2$ threshold 701 as inputs and a first alarm output 712. The threshold detector 710 changes the state of the first alarm output 712 when the value of the slow $SpO_2$ measurement 412 crosses the $SpO_2$ threshold 701. For example, the first alarm output 712 changes state to trigger an alarm when the slow $SpO_2$ measurement 412 becomes less than the $SpO_2$ threshold 701.

As shown in FIG. 7, the pattern extractor 720 has a fast $SpO_2$ measurement 422 and a pattern threshold 734 as inputs and an extracted pattern output 722. The pattern extractor 720 identifies features of the fast $SpO_2$ measurement 422 that may be used for pattern matching. Features may be, for example, the number of times the fast $SpO_2$ measurement 422 crosses the pattern threshold 734 within a certain time period, or the duration of each time period that the fast $SpO_2$ measurement 422 is less than the pattern threshold 734, to name a few. The pattern memory 730 has a pattern selection input 705 and a reference pattern output 732. The pattern memory 730 stores values for particular features that are identified by the pattern extractor 720. The reference pattern output 732 transfers these stored values to the pattern comparator 740. The pattern memory 730 may be nonvolatile and one or more patterns may be stored at the time of manufacture or downloaded subsequently via a data input (not shown). One of multiple patterns may be determined via the pattern selection input 705, by a user or by a separate process, for example. The pattern threshold 734 may be generated in response to the pattern selection input 705 or in conjunction with a selected reference pattern 732.

Also shown in FIG. 7, the pattern comparator 740 has the extracted pattern 722 and the reference pattern 732 as inputs and generates a second alarm output 742. That is, the pattern comparator 740 matches extracted measurement features provided by the pattern extractor 720 with selected features retrieved from pattern memory 730, changing the state of the second alarm output 742 accordingly. For example, the second alarm output 742 changes state to trigger an alarm when features of the fast $SpO_2$ measurement 422 match the reference pattern output 732. Advantageously, the pattern recognition alarm indicator 320 reduces missed events by supplementing the threshold-based first alarm output 712 responsive to the slow $SpO_2$ measurement 412 with a pattern-based second alarm output 742 responsive to detail in the fast $SpO_2$ measurement 422. In this manner, if a patient's oxygen saturation is, for example, irregular or intermittent, the second alarm output 742 may trigger a caregiver alert when the first alarm output 712 does not, as described in further detail with respect to FIG. 8, below.

Figure 8:
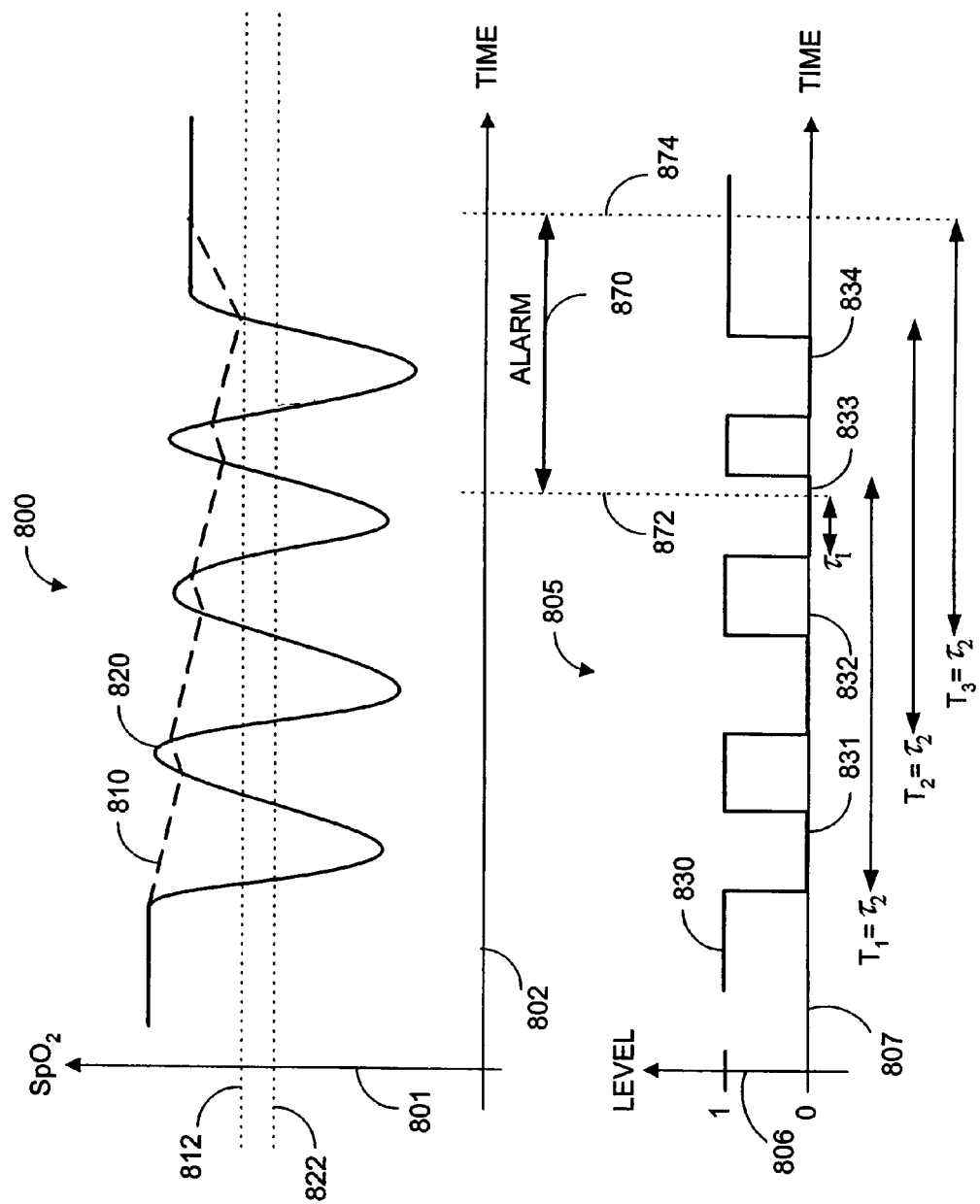
FIG. 8 is a graph of oxygen saturation versus time illustrating the pattern recognition alarm indicator according to FIG. 7.

FIG. 8 illustrates operation of a pattern recognition alarm indicator 320 (FIG. 7), as described above. A graph 800 has an $SpO_2$ axis 801 and a time axis 802. The graph 800 shows a $SpO_2$ plot versus time 810 corresponding to the slow $SpO_2$ measurement 412 (FIG. 7). Shown along the time axis 802 is a constant $SpO_2$ value 812 corresponding to the $SpO_2$ threshold 701 (FIG. 7). Due to the short duration of irregular and intermittent drops in $SpO_2$, the slow $SpO_2$ measurement 810 does not fall below the $SpO_2$ threshold 812. Thus, the first alarm output 712 (FIG. 7) does not trigger an alarm in this example.

Also shown in FIG. 8, the graph 800 shows a $SpO_2$ plot versus time 820 corresponding to the fast $SpO_2$ measurement 422 (FIG. 7). Shown along the time axis 802 is a constant $SpO_2$ value 822 corresponding to the pattern threshold 734 (FIG. 7). A corresponding graph 805 has a logic level axis 806 and a time axis 807. The graph 805 shows a logic level plot versus time 830 corresponding to the extracted pattern output 722 (FIG. 7). The logic level plot 830 has a "1" level when the fast $SpO_2$ plot 820 is above the pattern threshold 822 and a "0" level when the fast $SpO_2$ plot 820 is below the pattern threshold 822. In this manner, the logic level plot 830 indicates the number and duration of times the fast $SpO_2$ plot 820 falls below a threshold value 822.

Further shown in FIG. 8, an alarm interval 870 along the time axis 802 corresponds to an alarm period indicated by the pattern comparator 740 (FIG. 7). This alarm interval 870 occurs after a reference pattern 732 (FIG. 7) is detected as matching an extracted pattern 722 (FIG. 7) and ends, correspondingly, when there is no longer a match. For example, assume that the reference pattern output 732 (FIG. 7) has the alarm criteria that at least three below threshold periods of minimum duration $\tau_1$ must occur during a maximum period $\tau_2$, where the value of $\tau_1$ and $\tau_2$ are illustrated along the time axis 807. The below threshold time periods 831–834 are each greater in duration than $\tau_2$ and a first set of three, below-threshold time periods 831–833 occurs within a time period $T_1=\tau_2$, as illustrated. Thus, the alarm interval beginning 872 is triggered by the second alarm output 742 (FIG. 7). A second set of three, below-threshold time periods 832–834 also occurs within a time period $T_2=\tau_2$, as illustrated. Thus, the alarm interval 870 continues. There is no third set of three, below-threshold time periods. Thus, after the end of the time interval $T_3=\tau_2$, the alarm interval end 874 is triggered. This example illustrates how the pattern recognition alarm indicator 320 (FIG. 7) can trigger an alarm on an event, such as a period of irregular heartbeats, that might be missed by a threshold-based alarm responsive to the slow $SpO_2$ measurement 412.

Although some alarm processor embodiments were described above in terms of pulse oximetry and oxygen saturation measurements, one of ordinary skill in the art will recognize that an alarm processor as disclosed herein is also applicable to the measurement and monitoring of other blood constituents, for example blood glucose and total hemoglobin to name a few, and other physiological parameters such as blood pressure, pulse rate, respiration rate, and EKG to name a few.

A parallel measurement alarm processor has been disclosed in detail in connection with various embodiments. These embodiments are disclosed by way of examples only and are not to limit the scope of the claims that follow. One of ordinary skill in the art will appreciate many variations and modifications.

What is claimed is:

1. A method of activating an alarm on a pulse oximeter capable of determining a blood oxygen saturation measurement, the method comprising:

determining a smoothed measurement of blood oxygen saturation from a signal input responsive to a blood oxygen saturation of body tissue at a measurement site on a patient;

determining a predictive measurement of blood oxygen saturation from the signal input;

suppressing an alarm when said oxygen saturation is in a normal range or recovering toward the normal range; and activating an alarm when said oxygen saturation is below the normal range and is not recovering toward the normal range.

2. The method of claim 1, wherein the suppressing comprises suppressing the alarm when the smoothed measurement is above a threshold.

3. The method of claim 1, wherein the suppressing comprises suppressing the alarm when the predictive measurement is positive.

4. The method of claim 1, wherein the activating comprises activating the alarm when the smoothed measurement is below a threshold and when the predictive measurement is non-positive.

5. A pulse oximeter which activates an alarm, the pulse oximeter comprising:

a signal input responsive to a blood oxygen saturation of body tissue at a measurement site on a patient;

a first parameter processor capable of receiving the signal input and capable of determining a first measurement of the blood oxygen saturation;

a first comparator capable of determining how the first measurement relates to a first predetermined characteristic;

a second parameter processor capable of receiving the signal input and capable of determining a second measurement of the blood oxygen saturation, wherein the determination of the second measurement is different from the determination of the first measurement;

a second comparator capable of determining how the second measurement relates to a second predetermined characteristic;

an alarm capable of being activated based on the relationship between the first measurement and the first predetermined characteristic or based on the relationship between the second measurement and the second predetermined characteristic.

6. The pulse oximeter of claim 5, wherein the first parameter processor is capable of determining the first measurement comparatively slow, and wherein the second parameter processor is capable of determining the second measurement comparatively fast.

7. The pulse oximeter of claim 5, wherein the first measurement comprises a smoothed measurement.

8. The pulse oximeter of claim 5, wherein the second measurement comprises a predictive measurement.

9. The pulse oximeter of claim 5, wherein the first measurement comprises a smoothed measurement; wherein the second measurement comprises a predictive measurement; and wherein the alarm is not activated when the smoothed measurement is above a threshold or when the predictive measurement is positive, thereby suppressing alarms when said oxygen saturation is in a normal range or recovering toward a normal range.

10. The pulse oximeter of claim 5, wherein the first measurement comprises a smoothed measurement; wherein the second measurement comprises a predictive measurement; and wherein the alarm is asserted when the smoothed measurement is below a threshold and when the predictive measurement is non-positive, thereby asserting alarms when said oxygen saturation is below normal and is not recovering toward a normal range.

11. A method of activating an alarm on a pulse oximeter capable of determining a blood oxygen saturation measurement, the method comprising:

receiving a signal input responsive to a blood oxygen saturation of body tissue at a measurement site on a patient;

determining at least one of a first measurement of the blood oxygen saturation and a second measurement of the blood oxygen saturation, wherein the determination of the second measurement is different from the determination of the first measurement;

determining at least one of how the first measurement relates to a first predetermined characteristic and how the second measurement relates to a second predetermined characteristic;

activating an alarm based on at least one of the relationship between the first measurement and the first predetermined characteristic or the relationship between the second measurement and the second predetermined characteristic.

* * * * *